US012196752B2

(12) United States Patent
Fukuyama

(10) Patent No.: US 12,196,752 B2
(45) Date of Patent: Jan. 14, 2025

(54) METHOD FOR ANALYZING MICROORGANISM

(71) Applicant: SHIMADZU CORPORATION, Kyoto (JP)

(72) Inventor: Yuko Fukuyama, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 18/235,943

(22) Filed: Aug. 21, 2023

(65) Prior Publication Data
US 2023/0393134 A1 Dec. 7, 2023

Related U.S. Application Data

(62) Division of application No. 17/232,258, filed on Apr. 16, 2021, now Pat. No. 11,774,448.

(30) Foreign Application Priority Data

Apr. 23, 2020 (JP) ................................ 2020-076955

(51) Int. Cl.
G01N 33/569 (2006.01)
G01N 33/68 (2006.01)
H01J 49/00 (2006.01)

(52) U.S. Cl.
CPC ... *G01N 33/56916* (2013.01); *G01N 33/6851* (2013.01); *H01J 49/0036* (2013.01)

(58) Field of Classification Search
None
See application file for complete search history.

(56) References Cited

U.S. PATENT DOCUMENTS

2020/0300862 A1 9/2020 Tamura et al.

FOREIGN PATENT DOCUMENTS

CN 109313161 A 2/2019
JP 2015-184020 A 10/2015

OTHER PUBLICATIONS

Japanese Office Action dated Apr. 23, 2023 in Japanese Application No. 2020-076955.
(Continued)

Primary Examiner — Xiaoyun R Xu
(74) Attorney, Agent, or Firm — Sughrue Mion, PLLC

(57) ABSTRACT

A method for analyzing a microorganism including an identification step for determining which of *Abony* and *Pakistan* which are two serotypes of *Salmonella* bacteria is contained in a sample which contains either *Abony* or *Pakistan*, based on the presence or absence of a peak (or peaks) at a predetermined mass-to-charge ratio (or ratios) in a mass spectrum obtained by a mass spectrometric analysis of the sample, or a method for analyzing a microorganism including an identification step for determining which of *Minnesota*, *Infantis* and *Brandenburg* which are three serotypes of *Salmonella* bacteria is contained in a sample which contains *Minnesota*, *Infantis* or *Brandenburg*, based on the presence or absence of a peak (or peaks) at a predetermined mass-to-charge ratio (or ratios) in a mass spectrum obtained by a mass spectrometric analysis of the sample, or a method for analyzing a microorganism including an identification step for determining which of Schwarzengrund and Montevideo which are two serotypes of *Salmonella* bacteria is contained in a sample which contains either Schwarzengrund or Montevideo, based on the presence or absence of a peak (or peaks) at a predetermined mass-to-charge ratio (or ratios) in a mass spectrum obtained by a mass spectrometric analysis of the sample.

3 Claims, 4 Drawing Sheets

(56) References Cited

OTHER PUBLICATIONS

Teruyo Ojima-Kato et al., "Application of proteotyping Strain Solution™ ver. 2 software and theoretically calculated mass database in MALDI-TOF MS typing of *Salmonella* serotype", Applied Microbiology and Biotechnology, 2017, pp. 8557-8569, vol. 101, issue 23-24.

Chinese Office Action dated Jan. 12, 2024 in Application No. 202110439668.6.

METHOD FOR ANALYZING MICROORGANISM

CROSS REFERENCE TO RELATED APPLICATIONS

This application is a Divisional application of U.S. application Ser. No. 17/232,258, filed Apr. 16, 2021, which is based on Japanese Patent Applications No. 2020-076955 filed on Apr. 23, 2020, the contents of which are incorporated herein by reference.

TECHNICAL FIELD

The present invention relates to a method for analyzing a microorganism.

BACKGROUND ART

A matrix assisted laser desorption/ionization method, which is one type of ionization method in mass spectrometry, is an ionization method for analyzing a substance that barely absorbs laser light, or a substance that is likely to be damaged by laser light, such as proteins. A matrix substance, which considerably absorbs laser light and is thereby easily ionized, is mixed with a substance to be analyzed, and the mixture is irradiated with laser light to ionize the substance to be analyzed. Typically, the matrix substance is prepared in the form of a solution and is mixed with the substance to be analyzed. The solvent in the solution is subsequently vaporized to obtain a dried matrix in the form of a crystal containing the substance to be analyzed. Then, the mixture is irradiated with laser light, whereby the matrix substance absorbs the energy of the laser light and becomes rapidly heated to be ultimately vaporized. The substance to be analyzed is also vaporized with the matrix substance. Through this process, the substance to be analyzed becomes ionized.

A mass spectrometer using such a MALDI method (MALDI-MS) can analyze a high-molecular compound, such as a protein, without causing a significant dissociation of the compound, and is also suitable for microanalysis. Therefore, this type of mass spectrometer has been widely used in the area of life science. One application of the MALDI-MS in the area of life science is the identification of microorganisms using MALDI-MS. This is a method in which a microorganism is identified based on a mass spectrum pattern obtained using a test microorganism. Since this method can provide analysis results within a short period of time, the identification of a microorganism can be conveniently and speedily performed.

For example, a representative causative organism of food poisoning is *Salmonella*, which is a group of rod-shaped gram-negative facultatively anaerobic bacteria of the family Enterobacteriaceae. There are three species belonging to *Salmonella*: *Salmonella* (which is hereinafter abbreviated as "*S.*") *enterica*, *S. bongori* and *S. subterranea*. *S. enterica* is further divided into six subspecies. Many of the pathogenic *Salmonella* causative of food poisoning belong to *S. enterica* subsp. *enterica*. This subspecies is further divided into a large number of serotypes. Determining the species, subspecies and serotypes of *Salmonella* bacteria is important for elucidating the infection route of food poisoning and preventing the infection. Therefore, in recent years, attempts have been made to identify *Salmonella* bacteria using MALDI-MS.

CITATION LIST

Non Patent Literature

Non Patent Literature 1: Applied Microbiology and Biotechnology, Vol. 101, issue 23-24, pp. 8557-8569, 2017

SUMMARY OF INVENTION

Technical Problem

Determination of the species, subspecies and serotypes of *Salmonella* bacteria by MALDI-MS is achieved by detecting a biomarker peak, i.e., a peak whose position (mass-to-charge ratio; m/z value) and height (peak intensity; mV value) in the mass spectrum vary among bacterial bodies of different species, subspecies and serotypes. For the identification of microorganisms including bacteria, a protein peak is often used as a biomarker peak (see Non Patent Literature 1).

For many proteins in closely related microorganisms, it is normally the case that a peak originating from the same protein appears at the same mass-to-charge ratio m/z or within a narrow range of mass-to-charge ratios. Therefore, for an accurate identification of *Salmonella* bacteria at the level of serotype, it is not enough to select a peak originating from one protein as a biomarker peak; it is necessary to select peaks originating from a plurality of appropriate kinds of proteins for the serotype concerned. Additionally, there are only a limited number of serotypes which are known to be identifiable through the use of biomarker peaks. Identifying an even greater number of serotypes has been desired.

For example, Non Patent Literature 1 discloses a method in which the values of the mass-to-charge ratios of peaks originating from 12 kinds of proteins are read from a mass spectrum acquired by a mass spectrometric analysis of a sample containing microorganisms, and the serotype of *Salmonella* to which the microorganism contained in the sample belongs is determined from those values. However, in some cases, the use of the peaks originating from the 12 kinds of proteins as marker peaks can merely show that the serotype of the microorganism is among a plurality of specific serotypes of *Salmonella* bacteria, without specifically demonstrating which of those serotypes is the actual serotype.

The problem to be solved by the present invention is to enable accurate identification of a specific serotype of *Salmonella* bacteria in a method for analyzing a microorganism using a MALDI-MS.

Solution to Problem

The present invention developed for solving the previously described problem provides a method for analyzing a microorganism including:

an identification step for determining which of *Abony* and *Pakistan* which are two serotypes of *Salmonella* bacteria is contained in a sample which contains either *Abony* or *Pakistan*, based on the presence or absence of a peak (or peaks) at a predetermined mass-to-charge ratio (or ratios) in a mass spectrum obtained by a mass spectrometric analysis of the sample, where the value or values of the predetermined mass-to-charge ratio or ratios are selected from the group consisting of 3028, 3119, 4166, 5487, 5507, 5924, 6011, 6095, 6238, 6261, 6369, 6720, 6725, 6933, 7272, 7453, 7480, 7589, 7858, 7903, 8053, 8129, 8330, 8461, 8536, 8546, 8634, 8687, 9669, 9912, 10956, 11499, 11506, 11847, 12276, 13366, 13373, 13435, 13444, 15714, 15803 and 15990 as well as any combination of these values.

The present invention developed for solving the previously described problem also provides a method for analyzing a microorganism including:

an identification step for determining which of *Minnesota, Infantis* and *Brandenburg* which are three serotypes of *Salmonella* bacteria is contained in a sample which contains *Minnesota, Infantis* or *Brandenburg*, based on the presence or absence of a peak (or peaks) at a predetermined mass-to-charge ratio (or ratios) in a mass spectrum obtained by a mass spectrometric analysis of the sample, where the value or values of the predetermined mass-to-charge ratio or ratios are selected from the group consisting of 6094, 6483, 6689, 6719, 6872, 7858, 7940, 7948, 9322, 10667, 10990, 11808, 11821, 11848, 11857, 12209, 13367, 13376, 13406, 13445, 13476, 14882, 15716, 15803, 15878, 15895, 15991, 17713, 17735, 17813, 17835, 18972, 19127, 20766 and 20838 as well as any combination of these values.

The present invention developed for solving the previously described problem also provides a method for analyzing a microorganism including:

an identification step for determining which of Schwarzengrund and Montevideo which are two serotypes of *Salmonella* bacteria is contained in a sample which contains either Schwarzengrund or Montevideo, based on the presence or absence of a peak (or peaks) at a predetermined mass-to-charge ratio (or ratios) in a mass spectrum obtained by a mass spectrometric analysis of the sample, where the value or values of the predetermined mass-to-charge ratio or ratios are selected from the group consisting of 5096, 6699, 6733, 6830, 9034, 12262, 12276, 13074, 15820, 15835 and 19001 as well as any combination of these values.

Advantageous Effects of Invention

According to the present invention, if the sample contains a kind of bacteria which is *Abony* or *Pakistan* which are two serotypes of *Salmonella* bacteria, it is possible to correctly determine which of the two aforementioned serotypes is the serotype of the bacteria. If the sample contains a kind of bacteria which is *Minnesota, Infantis* or *Brandenburg* which are three serotypes of *Salmonella* bacteria, it is possible to correctly determine which of the three aforementioned serotypes is the serotype of the bacteria. If the sample contains a kind of bacteria which is Schwarzengrund or Montevideo which are two serotypes of *Salmonella* bacteria, it is possible to correctly determine which of the two aforementioned serotypes is the serotype of the bacteria.

DESCRIPTION OF EMBODIMENTS

Figure 1:
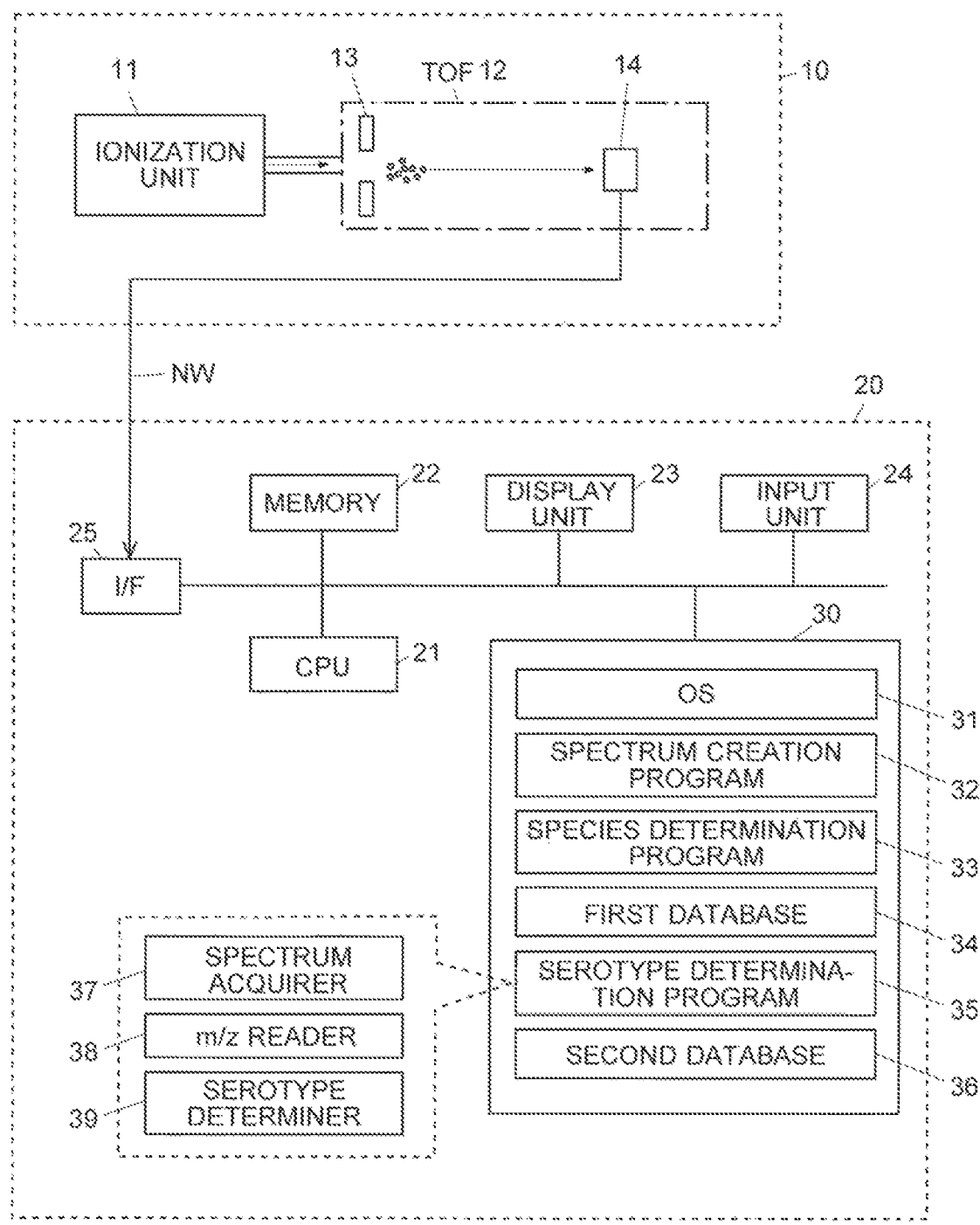
FIG. 1 is a schematic overall configuration diagram of a microorganism-analyzing system used for a method for analyzing a microorganism according to the present invention.
Figure 2:
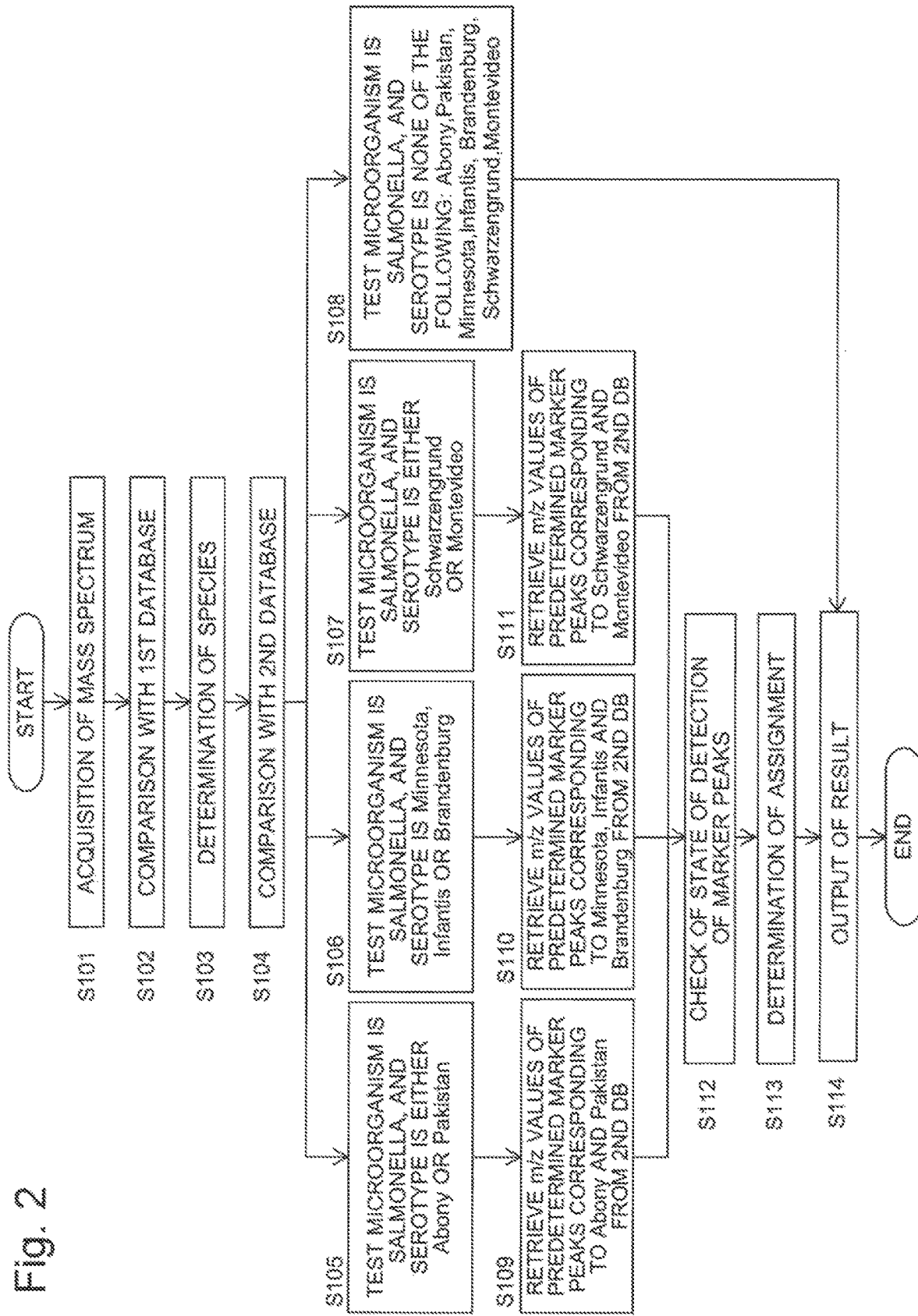
FIG. 2 is a flowchart showing one example of the procedure of the method for analyzing a microorganism.

The target of the method for analyzing a microorganism according to the present invention is a sample about which it is previously known that the microorganisms contained in the sample include a kind of bacteria belonging to one of the three groups of serotypes of *Salmonella*. The three groups of serotypes are: the group consisting of *Abony* and *Pakistan* which are two serotypes (hereinafter called the first group); the group consisting of *Minnesota, Infantis* and *Brandenburg* which are three serotypes (hereinafter called the second group); and the group consisting of Schwarzengrund and Montevideo which are two serotypes (hereinafter called the third group). That is to say, the target of the analysis is (a) a sample about which it is previously known that the sample contains a kind of *Salmonella* bacteria belonging to the first group but it is unknown which of *Abony* and *Pakistan* is the serotype of the bacteria, or (b) a sample about which it is previously known that the sample contains a kind of *Salmonella* bacteria belonging to the second group but it is unknown which of *Minnesota, Infantis* and *Brandenburg* is the serotype of the bacteria, or (c) a sample about which it is previously known that the sample contains a kind of *Salmonella* bacteria belonging to the third group but it is unknown which of Schwarzengrund and Montevideo is the serotype of the bacteria.

That is to say, a method for analyzing a microorganism according to the present invention is a method for analyzing a microorganism including:

an identification step for determining which of *Abony* and *Pakistan* which are two serotypes of *Salmonella* bacteria is contained in a sample which contains either *Abony* or *Pakistan*, based on the presence or absence of a peak (or peaks) at a predetermined mass-to-charge ratio (or ratios) in a mass spectrum obtained by a mass spectrometric analysis of the sample, where the value or values of the predetermined mass-to-charge ratio or ratios are selected from the group consisting of 3028, 3119, 4166, 5487, 5507, 5924, 6011, 6095, 6238, 6261, 6369, 6720, 6725, 6933, 7272, 7453, 7480, 7589, 7858, 7903, 8053, 8129, 8330, 8461, 8536, 8546, 8634, 8687, 9669, 9912, 10956, 11499, 11506, 11847, 12276, 13366, 13373, 13435, 13444, 15714, 15803 and 15990 as well as any combination of these values. In particular, the value (or values) of the predetermined mass-to-charge ratio or ratios should preferably be selected from the group consisting of 3119, 4166, 5487, 6238, 6720, 7858, 8330, 8536, 8687, 9912, 12276, 15714, 15803 and 15990 as well as any combination of these values.

The state of the peak detection for *Abony* and *Pakistan* which are two serotypes corresponding to the previously mentioned mass-to-charge ratios are shown in Tables 1 and 2. In the present invention, the peaks at the mass-to-charge ratios shown in Table 1 or 2 are used as marker peaks, and which of the two serotypes *Abony* and *Pakistan* is the actual serotype is determined by checking the state of the detection of those peaks.

TABLE 1

| Mass-to-Charge Ratio (m/z) | S. Abony | S. Pakistan |
|---|---|---|
| 3028.3 | ○ | x |
| 3119.4 | ○ | x |
| 4165.7 | ○ | x |
| 5487.4 | x | ○ |
| 5506.7 | x | ○ |
| 5924.3 | ○ | x |
| 6010.9 | ○ | x |
| 6095.3 | ○ | x |
| 6238.3 | ○ | x |
| 6261.2 | x | ○ |
| 6369.4 | ○ | x |
| 6719.7 | ○ | x |
| 6724.6 | x | ○ |
| 6933.3 | x | ○ |
| 7272.2 | x | ○ |
| 7453.4 | ○ | x |
| 7480.2 | x | ○ |
| 7588.5 | ○ | x |
| 7858.2 | x | ○ |
| 7902.9 | ○ | x |
| 8053.4 | x | ○ |
| 8129.3 | x | ○ |
| 8329.5 | ○ | x |
| 8460.9 | ○ | x |
| 8536.2 | ○ | x |
| 8546.2 | x | ○ |
| 8633.7 | ○ | x |
| 8687.2 | ○ | x |
| 9669.0 | x | ○ |
| 9911.9 | ○ | x |
| 10956.1 | ○ | x |
| 11498.9 | x | ○ |
| 11505.5 | ○ | x |
| 11847.4 | ○ | x |
| 12276.2 | ○ | x |
| 13365.7 | ○ | x |

TABLE 1-continued

| Mass-to-Charge Ratio (m/z) | S. Abony | S. Pakistan |
|---|---|---|
| 13372.6 | x | ○ |
| 13435.4 | ○ | x |
| 13444.3 | x | ○ |
| 15713.9 | x | ○ |
| 15803.3 | ○ | x |
| 15990.2 | ○ | x |

TABLE 2

| Mass-to-Charge Ratio (m/z) | S. Abony | S. Pakistan |
|---|---|---|
| 3119.4 | ○ | x |
| 4165.7 | ○ | x |
| 5487.4 | x | ○ |
| 6238.3 | ○ | x |
| 6719.7 | ○ | x |
| 7858.2 | x | ○ |
| 8329.5 | ○ | x |
| 8536.2 | ○ | x |
| 8687.2 | ○ | x |
| 9911.9 | ○ | x |
| 12276.2 | ○ | x |
| 15713.9 | x | ○ |
| 15803.3 | ○ | x |
| 15990.2 | ○ | x |

Another method for analyzing a microorganism according to the present invention is a method for analyzing a microorganism including:

an identification step for determining which of *Minnesota*, *Infantis* and *Brandenburg* which are three serotypes of *Salmonella* bacteria is contained in a sample which contains *Minnesota*, *Infantis* or *Brandenburg*, based on the presence or absence of a peak (or peaks) at a predetermined mass-to-charge ratio (or ratios) in a mass spectrum obtained by a mass spectrometric analysis of the sample, where the value or values of the predetermined mass-to-charge ratio or ratios are selected from the group consisting of 6094, 6483, 6689, 6719, 6872, 7858, 7940, 7948, 9322, 10667, 10990, 11808, 11821, 11848, 11857, 12209, 13367, 13376, 13406, 13445, 13476, 14882, 15716, 15803, 15878, 15895, 15991, 17713, 17735, 17813, 17835, 18972, 19127, 20766 and 20838 as well as any combination of these values. In particular, the value or values of the predetermined mass-to-charge ratio or ratios should preferably be selected from the group consisting of 6483, 7940, 10990, 11808, 11821, 11848, 11857, 12209, 13406, 13445, 15803, 15878, 15895, 17713 and 17735 as well as any combination of these values.

The state of the peak detection for *Minnesota*, *Infantis* and *Brandenburg* which are three serotypes corresponding to the previously mentioned mass-to-charge ratios are shown in Tables 3 and 4. In the present invention, the peaks at the mass-to-charge ratios shown in Table 3 or 4 are used as marker peaks, and which of the three serotypes *Minnesota*, *Infantis* and *Brandenburg* is the actual serotype is determined by checking the state of the detection of those peaks.

TABLE 3

| Mass-to-Charge Ratio (m/z) | S. Minnesota I | S. Minnesota II | S. Infantis I | S. Infantis II | S. Brandenburg I |
|---|---|---|---|---|---|
| 6094.0 | x | x | ○ | ○ | ○ |
| 6483.3 | ○ | ○ | x | ○ | ○ |
| 6688.5 | ○ | ○ | x | ○ | ○ |
| 6719.0 | x | x | ○ | x | x |
| 6872.2 | ○ | ○ | x | ○ | ○ |
| 7857.5 | ○ | x | x | x | x |
| 7939.5 | x | x | ○ | x | ○ |
| 7947.5 | ○ | ○ | x | ○ | x |
| 9322.0 | x | x | x | ○ | ○ |
| 10667.0 | x | x | x | ○ | x |
| 10990.3 | x | x | ○ | x | x |
| 11807.5 | ○ | ○ | x | ○ | ○ |
| 11821.4 | x | x | ○ | x | x |
| 11847.8 | ○ | ○ | x | ○ | ○ |
| 11856.7 | x | x | ○ | x | x |
| 12209.3 | x | x | ○ | x | x |
| 13366.5 | ○ | x | ○ | ○ | x |
| 13376.0 | x | ○ | x | x | ○ |
| 13406.3 | x | x | x | ○ | x |
| 13445.2 | ○ | ○ | x | ○ | ○ |
| 13475.9 | x | ○ | x | x | ○ |
| 14882.1 | x | x | x | x | ○ |
| 15715.6 | ○ | x | x | x | x |
| 15803.1 | x | x | ○ | x | x |
| 15878.4 | x | x | ○ | x | ○ |
| 15894.7 | ○ | ○ | x | ○ | x |
| 15991.1 | x | ○ | ○ | ○ | ○ |
| 17713.0 | ○ | ○ | x | ○ | ○ |
| 17734.5 | x | x | ○ | x | x |
| 17812.8 | ○ | ○ | x | ○ | ○ |
| 17835.0 | x | x | ○ | x | x |
| 18972.3 | x | x | ○ | ○ | ○ |
| 19127.0 | x | x | ○ | x | x |
| 20765.8 | ○ | ○ | ○ | x | x |
| 20837.6 | x | x | x | x | ○ |

TABLE 4

| Mass-to-Charge Ratio (m/z) | S. Minnesota I | S. Minnesota II | S. Infantis I | S. Infantis II | S. Brandenburg I |
|---|---|---|---|---|---|
| 6483.3 | ○ | ○ | x | ○ | ○ |
| 7939.5 | x | x | ○ | x | ○ |
| 10990.3 | x | x | ○ | x | x |
| 11807.5 | ○ | ○ | x | ○ | ○ |
| 11821.4 | x | x | ○ | x | x |
| 11847.8 | ○ | ○ | x | ○ | ○ |
| 11856.7 | x | x | ○ | x | x |
| 12209.3 | x | x | ○ | x | x |
| 13406.3 | x | x | x | ○ | x |
| 13445.2 | ○ | ○ | x | ○ | ○ |
| 15803.1 | x | x | ○ | x | x |
| 15878.4 | x | x | ○ | x | ○ |
| 15894.7 | ○ | ○ | x | ○ | x |
| 17713.0 | ○ | ○ | x | ○ | ○ |
| 17734.5 | x | x | ○ | x | x |

Another method for analyzing a microorganism according to the present invention is a method for analyzing a microorganism including:

an identification step for determining which of Schwarzengrund and Montevideo which are two serotypes of *Salmonella* bacteria is contained in a sample which contains either Schwarzengrund or Montevideo, based on the presence or absence of a peak (or peaks) at a predetermined mass-to-charge ratio (or ratios) in a mass spectrum obtained by a mass spectrometric analysis of the sample, where the value or values of the predetermined mass-to-charge ratio or ratios are selected from the group consisting of 5096, 6699, 6733, 6830, 9034, 12262, 12276, 13074, 15820, 15835 and 19001 as well as any combination of these values. In particular, the value or values of the predetermined mass-to-charge ratio or ratios should preferably be selected from the group consisting of 5096, 6699, 6733, 6830, 9034, 12276, 15820 and 15835 as well as any combination of these values.

The state of the peak detection for Schwarzengrund and Montevideo which are two serotypes corresponding to the previously mentioned mass-to-charge ratios are shown in Tables 5 and 6. In the present invention, the peaks at the mass-to-charge ratios shown in Table 5 or 6 are used as marker peaks, and which of the two serotypes Schwarzengrund and Montevideo is the actual serotype is determined by checking the state of the detection of those peaks.

TABLE 5

| Mass-to-Charge Ratio (m/z) | S. Schwarzengrund | S. Montevideo |
|---|---|---|
| 5096.4 | x | ○ |
| 6699.2 | ○ | x |
| 6733.1 | x | ○ |
| 6830.1 | ○ | x |
| 9034.4 | ○ | x |
| 12261.9 | x | ○ |
| 12276.1 | ○ | x |
| 13074.0 | x | ○ |
| 15819.5 | ○ | x |
| 15834.5 | x | ○ |
| 19001.0 | x | ○ |

TABLE 6

| Mass-to-Charge Ratio (m/z) | S. Schwarzengrund | S. Montevideo |
|---|---|---|
| 5096.4 | x | ○ |
| 6699.2 | ○ | x |
| 6733.1 | x | ○ |
| 6830.1 | ○ | x |
| 9034.4 | ○ | x |
| 12276.1 | ○ | x |
| 15819.5 | ○ | x |
| 15834.5 | x | ○ |

As for the criterion for the peak extraction in the previously described methods for analyzing a microorganism, either the first criterion or second criterion which will be described later may be used, although the criteria are not limited to these examples. Since the second criterion applies stricter conditions to the peak extraction than the first one, it is likely that using the second criterion decreases incorrect determinations. However, since the intensity ratio of the peaks may change depending on the strain or culture conditions, it is preferable to decide the use of the first or second criterion according to the purpose of the determination of the serotype. It is also possible to initially extract peaks according to the first criterion and further extract peaks which satisfy the second criterion among the initially extracted peaks. It is also possible to initially extract peaks according to the second criterion, and if it is still difficult to identify the target serotype, peaks which do not satisfy the second criterion but satisfy the first criterion may subsequently be extracted for identification. The value of the mass-to-charge ratio of each peak should be understood as a rough value and inclusive of a certain range of variation depending on the type of device for mass spectrometry, conditions of the analysis or other factors. Tables 1, 3 and 5 show the states of the peak detection using the first criterion, while Tables 2, 4 and 6 show the states of the peak detection using the second criterion. In each table, the circle indicates that a peak was detected, while the cross indicates that no peak was detected.

(1) First Criterion

In the case of a group consisting of two serotypes, a peak should be extracted (a) if the peak is detected with an S/N value equal to or greater than three in a mass spectrum obtained from a sample containing one of the two serotypes of *Salmonella* bacteria, while the same peak in a mass spectrum obtained from a sample containing the other serotype of *Salmonella* bacteria is not detected, or is detected with an S/N value not greater than one fifth of the S/N value of the first mass spectrum, or (b) if the peak in one mass spectrum is detected with an S/N value equal to or greater than three, while the same peak in the other mass spectrum is not detected, or is detected with an S/N value not greater than one tenth of the S/N value of the first mass spectrum and is accompanied by, or partially overlaps with, a nearby peak having a close value of the mass-to-charge ratio m/z.

In the case of a group consisting of three serotypes, a peak should be extracted (a) if the peak is detected with an S/N value equal to or greater than three in one of the three mass spectra obtained from three samples respectively containing any one of the three serotypes of *Salmonella* bacteria, while the same peak in the two other mass spectra is not detected, or is detected with an S/N value not greater than one fifth of the S/N value of the first mass spectrum, or (b) if the peak in one of the three mass spectra is detected with an S/N value equal to or greater than three, while the same peak on the two other mass spectra is not detected or is detected with an S/N value not greater than one tenth of the S/N value of the first mass spectrum and is accompanied by, or partially overlaps with, a nearby peak having a close value of the mass-to-charge ratio m/z.

(2) Second Criterion

In the case of a group consisting of two serotypes, a peak should be extracted if the peak is detected with an S/N value equal to or greater than ten in a mass spectrum obtained from a sample containing one of the two serotypes of *Salmonella* bacteria, while the same peak in a mass spectrum obtained from a sample containing the other serotype of *Salmonella* bacteria is not detected, or is detected with an S/N value not greater than one tenth of the S/N value of the first mass spectrum.

In the case of a group consisting of three serotypes, a peak should be extracted if the peak is detected with an S/N value equal to or greater than ten in one of the three mass spectra obtained from three samples respectively containing any one of the three serotypes of *Salmonella* bacteria, while the same peak in the two other mass spectra is not detected, or is detected with an S/N value not greater than one tenth of the S/N value of the first mass spectrum.

In any case, a peak extracted based on the second criterion needs to be an isolated peak accompanied by neither a nearby peak nor partially overlapping peak which leads to an incorrect determination.

In this case, the m/z value should be evaluated, for example, with an accuracy of 800 ppm, or preferably 500 ppm. If a plurality of peaks are present within that accuracy, the peak having the closest m/z value should be selected as a marker peak.

The group to which a microorganism contained in a sample belongs among the first through third groups of *Salmonella* bacteria can be identified, for example, by using the values of the mass-to-charge ratios of the peaks originating from the 12 kinds of proteins (gns, YaiA, YibT, PPI, L25, L21, S8, L17, L15, S7, YciF and SodA) disclosed in Non Patent Literature.

In the method for analyzing a microorganism according to the present invention, the identification of one of the serotypes of bacteria in each group may be based on the presence or absence of a peak at a single mass-to-charge ratio. However, the identification accuracy will be improved if the identification of one of the serotypes of bacteria in each group is based on the presence or absence of the peaks at a plurality of mass-to-charge ratios.

As a mass spectrometer to be used for the method for analyzing a microorganism according to the present invention, a mass spectrometer using a matrix assisted laser desorption/ionization (MALDI) method (MALDI-MS) is preferable. As the MALDI-MS, a MALDI time-of-flight mass spectrometer (MALDI-TOFMS) can preferably be used. Since the MALDI-MS has an extremely wide range of measurable mass-to-charge ratios, a mass spectrum suited for an analysis of high-mass molecules, such as the proteins which are constituents of microorganisms, can be acquired.

Next, one embodiment of the microorganism-analyzing system to be used for the method for analyzing a microorganism according to the present invention is described.

FIG. 1 shows a schematic overall configuration of the microorganism-analyzing system. This system is roughly divided into a mass spectrometry unit 10 and a microorganism identification unit 20. The mass spectrometry unit 10 includes an ionization unit 11 configured to ionize molecules or atoms in a sample by matrix assisted laser desorption/ionization (MALDI) and a time-of-flight mass separator (TOF) 12 configured to separate various ions, ejected from the ionization unit 11, according to their mass-to-charge ratios.

The TOF 12 includes an extraction electrode 13 configured to extract ions from the ionization unit 11 and guide them into an ion flight space within the TOF 12, and a detector 14 configured to detect ions which have been mass-separated within the ion flight space.

The microorganism identification unit 20 is actually a workstation, personal computer or other types of computers, in which a central processing unit (CPU) 21, memory 22, display unit 23 (e.g., a liquid crystal display), input unit 24 (e.g., a keyboard and mouse), and storage unit 30 consisting of a large-capacity storage (e.g., a hard disk drive or solid state drive) are connected to each other. Stored in the storage unit 30 are an operating system (OS) 31, spectrum creation program 32, species determination program 33 and serotype determination program 35 (a program according to the present invention), as well as a first database 34 and second database 36. The microorganism identification unit 20 further includes an interface (T/F) 25 for controlling a direct connection to an external device as well as a connection with an external device through a local area network (LAN) or other types of networks. Through this interface 25, the microorganism identification unit 20 is connected with the mass spectrometry unit 10 by a network cable NW (or wireless LAN).

In FIG. 1, a spectrum acquirer 37, m/z reader 38 and serotype identifier 39 are shown, being linked to the serotype determination program 35. Each of those components is basically a functional means implemented at the software level by the CPU 21 executing the serotype determination program 35. The serotype determination program 35 does not need to be an independent program. There is no specific limitation on its form; for example, it may be a built-in function of the species determination program 33 or that of a program for controlling the mass spectrometry unit 10. As the species determination program 33, for example, a program configured to identify microorganisms by a conventional fingerprinting method may be used.

In the configuration in FIG. 1, the spectrum creation program 32, species determination program 33, serotype determination program 35, first database 34 and second database 36 are installed on a terminal device to be operated by users. Those components may be at least partially, or even entirely, installed on a separate device connected with the aforementioned terminal device via a computer network, with the separate device configured to perform the processing by those programs and/or access to those databases according to commands from the terminal device.

The first database 34 in the storage unit 30 holds a large number of mass lists related to known microorganisms. The mass list is a list of the mass-to-charge ratios of ions to be detected in a mass spectrometric analysis of a specific kind of microorganic cell. Along with the information of the mass-to-charge ratios, the list additionally includes at least the information of the classifications (family, genus, species, etc.) to which the microorganic cell belongs (classification information). Those mass lists should preferably be prepared based on actual measurement data obtained beforehand by actually performing mass spectrometric analyses of various kinds of microorganic cells using the same method for ionization and mass separation as used in the mass spectrometry unit 10.

When the mass lists are to be prepared from the actual measurement data, the peaks which appear within a predetermined mass-to-charge-ratio range are initially extracted from mass spectra obtained as the actual measurement data. Peaks which mainly originate from proteins can be extracted by setting the aforementioned mass-to-charge-ratio range at approximately 4000-30000, while unwanted peaks (noise) can be excluded by extracting each peak whose height (relative intensity) is equal to or higher than a predetermined threshold. A list of the mass-to-charge ratios (m/z) of the extracted peaks is created for each kind of cell and recorded in the first database 34 along with the aforementioned classification information and other related information. In order to reduce the variation in gene expression due to the culture conditions, the microorganic cells to be used for collecting the actual measurement data should preferably be cultured under previously normalized conditions.

The second database 36 in the storage unit 30 holds information concerning marker proteins for identifying, known kinds of microorganisms, by their serotypes which are classifications lower than the species. The information concerning the marker proteins includes at least the information of the mass-to-charge ratios (m/z) of the marker proteins in the known kinds of microorganisms. The second database 36 may also hold information concerning marker proteins for identifying known kinds of microorganisms by another sub-classification (e.g., subspecies, pathotype or strain) other than the serotype, or by other criteria.

The second database 36 in the present embodiment contains the values of the mass-to-charge ratios of peaks originating from 12 kinds of marker proteins (gns, YaiA, YibT, PPI, L25, L21, S8, L17, L15, S7, YciF and SodA) for determining the serotype of a test microorganism in the case where the microorganism is a kind of *Salmonella* bacteria (see Non Patent Literature 1), as well as information related to marker proteins for determining the serotype of a test microorganism whose serotype has been identified as belonging to one of the first through third groups of *Salmonella* bacteria. Specifically, this information includes the values of the mass-to-charge ratios of predetermined marker peaks for determining (a) which of the two serotypes belonging to the first group is when the serotype of a test microorganism has been identified as belonging to the first group, or (b) which of the three serotypes belonging to the second group is when the serotype of a test microorganism has been identified as belonging to the second group, or (c) which of the two serotypes belonging to the third group is when the serotype of a test microorganism has been identified as belonging to the third group (specifically, the combinations of the values of the mass-to-charge ratios shown in Tables 1-6).

The values of the mass-to-charge ratios of the marker proteins stored in the second database 36 should preferably be selected by comparing a calculation mass determined by translating the base sequence of each marker protein into an amino-acid sequence, and a mass-to-charge ratio detected by an actual measurement. The base sequences of the marker proteins may be determined by sequencing method, or they may be retrieved from public databases, e.g., a database at NCBI (National Center for Biotechnology Information). For the determination of the calculation mass from the amino-acid sequence, the cutting of the N-terminal methionine residue should preferably be taken into account as a post-translational modification. Specifically, if the second amino-acid residue to the last is Gly, Ala, Ser, Pro, Val, Thr or Cys, the theoretical value should be calculated on the assumption that the N-terminal methionine will be cut. Additionally, since the molecule to be actually observed with a MALDI-TOF MS is in a protonated form, the addition of the proton should also preferably be taken into account in determining the calculation mass (i.e., a theoretical values of the mass-to-charge ratio of ions to be obtained in an analysis of a protein with a MALDI-TOF MS).

Next, a procedure of the analysis of the serotype of *Salmonella* bacteria using the previously described microorganism-analyzing system is described with reference to the flowchart.

Initially, the user prepares a sample containing the constituents of a test microorganism, sets the sample in the mass spectrometry unit 10, and operates the same unit to perform the mass spectrometric analysis. The sample may be a cell extract, or cell constituents (e.g., ribosomal proteins) collected from the cell extract and purified. Bacterial bodies or cell suspension may also be used as they are.

The spectrum creation program 32 receives detection signals from the detector 14 via the interface 25, and creates a mass spectrum for the test microorganism based on the detection signals (Step 101).

Next, the species determination program 33 compares the mass spectrum of the test microorganism with the mass lists of known microorganisms recorded in the first database 34, and extracts a mass list of a known microorganism having a similar pattern of mass-to-charge ratios to that of the mass spectrum of the test microorganism, such as a mass list including a considerable number of peaks which coincide with those of the mass spectrum of the test microorganism within a predetermined margin of error (Step 102). The species determination program 33 subsequently searches the first database 34 for the classification information related to the mass list extracted in Step 102, to determine the organism species to which the known microorganism corresponding to the mass list belongs (Step 103). If the organism species is not *Salmonella*, the organism species is displayed on the display unit 23 as the organism species of the test microorganism (Step 114), and the analytical processing is completed. If the organism species is *Salmonella*, the analysis proceeds to the processing by the serotype determination program 35. In the case where it has been previously determined by another method that the sample contains *Salmonella* bacteria, and the analysis can directly proceed to the serotype determination program 35 without using the species determination program using the mass spectrum.

In the serotype determination program 35, the mass spectrum of the test microorganism is compared with the values of the mass-to-charge ratios of the marker proteins recorded in the second database, to identify the serotype of the test microorganism (Step 104). Specifically, the serotype determiner 39 initially reads, from the second database 36, the values of the mass-to-charge ratios of the peaks originating from the 12 aforementioned kinds of marker proteins (gns, YaiA, YibT, PPI, L25, L21, S8, L17, L15, S7, YciF and SodA). Subsequently, the spectrum acquirer 37 obtains the mass spectrum of the test microorganism prepared in Step 101. Then, for each marker protein, the m/z reader 38 selects a corresponding peak present in the mass spectrum within a mass-to-charge-ratio range related to the marker protein in the second database 36, and determines the serotype based on the values of the mass-to-charge ratios of the selected peaks.

If the determination result indicates that the serotype of the test microorganism is a serotype belonging to the first group (*Abony* or *Pakistan*; Step 105), the values of the mass-to-charge ratios of the predetermined marker peaks corresponding to the serotypes belonging to the first group are retrieved from the second database (Step 109).

If the determination result indicates that the serotype of the test microorganism is a serotype belonging to the second group (*Minnesota, Infantis* or *Brandenburg*; Step 106), the values of the mass-to-charge ratios of the predetermined marker peaks corresponding to the serotypes belonging to the second group are retrieved from the second database (Step 110).

If the determination result indicates that the serotype of the test microorganism is a serotype belonging to the third group (Schwarzengrund or Montevideo; Step 107), the values of the mass-to-charge ratios of the predetermined marker peaks corresponding to the serotypes belonging to the third group are retrieved from the second database (Step 111).

If the determination result indicates that the serotype of the test microorganism is a serotype which belongs to none of the first through third groups (Step 108), the serotype of the test microorganism is shown on the display unit 23 as a serotype which is none of the serotypes belonging to the first through third groups (Step 114).

After the serotype has been identified as belonging to one of the first through third groups, and the values of the mass-to-charge ratios of the predetermined marker peaks corresponding to the serotypes belonging to each group have been retrieved, the presence or absence of a peak is checked for each of the mass-to-charge-ratio ranges related to those values of the mass-to-charge ratios and stored in the second database 36 (Step 112). Based on the state of the presence or absence of the peaks, the serotype of the test microorganism is determined (Step 113), and the determination is shown on the display unit 23 as the identification result for the test microorganism (Step 114).

Example

Hereinafter described is an experiment conducted to prove the effect of the method for analyzing a microorganism according to the present embodiment. It should be noted that the following descriptions are merely illustrative and do not limit the present invention.

1. Culturing of *Salmonella* Bacteria

A total of seven kinds of *Salmonella* bacteria (*Salmonella enterica*), i.e., the two kinds of *Salmonella* bacteria belonging to the first group, the three kinds of *Salmonella* bacteria belonging to the second group, and the two kinds of *Salmonella* bacteria belonging to the third group, were cultured at 37 degrees Celsius for 20 hours using LB agar.

The kinds of *Salmonella* bacteria belonging to the first through third groups are as follows.

(1) First Group
  *S. abony*, NBRC100797
  *S. pakistan*, GTC09493
(2) Second Group
  *S. minnesota*, NBRC15182
  *S. infantis*, ATCC BAA-1675
  *S. brandenburg*, jfrlSe1402-3
(3) Third Group
  *S. schwarzengrund*, HyogoSO12004
  *S. montevideo*, jfrlSe1409-6

2. Preparation of Matrix Solutions

The following two kinds of matrix solutions were prepared.

(2-1) Sinapine acid (SA) as the matrix substance was dissolved in ethanol to obtain a matrix solution (saturated solution) with an SA content of 25 mg/mL. This matrix solution is hereinafter called "SA-1".

(2-2) SA, methylene diphosphonate (MDPNA) and decyl-β-D-maltopyranoside (DMP) as a surfactant were dissolved in an aqueous solution with an acetonitrile (ACN) content of 50% and trifluoroacetic acid (TFA) content of 0.6% to obtain a matrix solution with an SA content of 25 mg/mL, MDPNA content of 1%, and DMP content of 1 mM. This matrix solution is hereinafter called "SA-2".

The SA used for the matrix solutions SA-1 and SA-2 was a product of FUJIFILM Wako Pure Chemical Corporation. The MDPNA and DMP were products of Sigma-Aldrich Japan LLC.

3. Preparation of Matrix-Microorganism Suspension (3-1) From each of the 7 kinds of *Salmonella* bacteria cultured on LB agar, approximately 1 mg of sample was collected using a microbalance and put in a tube. The matrix solution SA-2 was added to the sample in the tube to obtain a solution with a bacteria concentration of 1 mg/0.075 mL ($1 \times 10^7$ CFU/µL), and this solution was suspended with a needle.

(3-2) Ultrasonic vibrations were applied to the tube for one minute. The obtained suspension was centrifuged (at 12000 rpm for 5 minutes) to obtain a centrifugation supernatant.

4. Analysis with MALDI-MS (4-1) The matrix solution SA-1 was dropped into the wells on a MALDI sample plate, at 0.5 µL per one well (precoating).

(4-2) Subsequently, the centrifugation supernatant was dropped into the wells precoated with the matrix solution SA-1, at 1 µL per one well, and was let to naturally dry.

(4-3) The MALDI sample plate obtained in (4-2) was set in a MALDI-MS (AXIMA Performance, manufactured by Shimadzu Corporation), and the measurement was performed in a linear mode (positive ion mode). All measurement data were acquired by a raster analysis. Raster analysis is an automatic measurement function provided in the previously mentioned mass spectrometer. In this technique, the sample in each well of the sample plate is irradiated with a predetermined number of laser shots at a predetermined number of points, to acquire mass spectrum data.

5. Extraction of Peaks

A self-calibration of *Salmonella* bacteria was applied to the measurement data (more specifically, a calibration process was performed using, as internal standards, some peaks that have already been assigned to specific *Salmonella* bacteria), and useful peaks for the identification of the serotype were extracted from the obtained mass spectrum. The values of the mass-to-charge ratios of the peaks originating from the 12 kinds of marker proteins shown in Non Patent Literature 1 were read from the extracted peaks, and the serotype of *Salmonella* bacteria to which the microorganism contained in the sample belonged was determined from the read values.

In the determination of the serotype using the 12 kinds of marker proteins, when it was determined that the microorganism was either *Abony* or *Pakistan* which are two serotypes of *Salmonella* bacteria, the state of the peak detection on the obtained mass spectrum was checked at one or more values of the mass-to-charge ratios selected from the group consisting of 3028, 3119, 4166, 5487, 5507, 5924, 6011, 6095, 6238, 6261, 6369, 6720, 6725, 6933, 7272, 7453, 7480, 7589, 7858, 7903, 8053, 8129, 8330, 8461, 8536, 8546, 8634, 8687, 9669, 9912, 10956, 11499, 11506, 11847, 12276, 13366, 13373, 13435, 13444, 15714, 15803 and 15990.

In the determination of the serotype using the 12 kinds of marker proteins, when it was determined that the microorganism was one of *Minnesota, Infantis* and *Brandenburg* which are three serotypes of *Salmonella* bacteria, the state of the peak detection on the obtained mass spectrum was checked at one or more values of the mass-to-charge ratios selected from the group consisting of 6094, 6483, 6689, 6719, 6872, 7858, 7940, 7948, 9322, 10667, 10990, 11808, 11821, 11848, 11857, 12209, 13367, 13376, 13406, 13445, 13476, 14882, 15716, 15803, 15878, 15895, 15991, 17713, 17735, 17813, 17835, 18972, 19127, 20766 and 20838.

In the determination of the serotype using the 12 kinds of marker proteins, when it was determined that the microorganism was either Schwarzengrund or Montevideo which are two serotypes of *Salmonella* bacteria, the state of the peak detection on the obtained mass spectrum was checked at one or more values of the mass-to-charge ratios selected from the group consisting of 5096, 6699, 6733, 6830, 9034, 12262, 12276, 13074, 15820, 15835 and 19001. The m/z values were evaluated with an accuracy of 800 ppm, or preferably 500 ppm. When a plurality of peaks were present within that accuracy, the peak having the closest m/z value was selected as the marker peak.

6. Results (1) First Group

The state of the peak detection at the previously listed mass-to-charge ratios (m/z values) was checked on the mass spectra obtained from two samples which respectively contained one of the two kinds of *Salmonella* bacteria belonging to the first group (*S. abony* and *S. pakistan*). The state of the detection was as shown in Tables 1 and 2. In Tables 1 and 2, the circle indicates that the marker peak at the mass-to-charge ratio concerned was detected, while the cross indicates that the marker peak was not detected.

Figure 3:
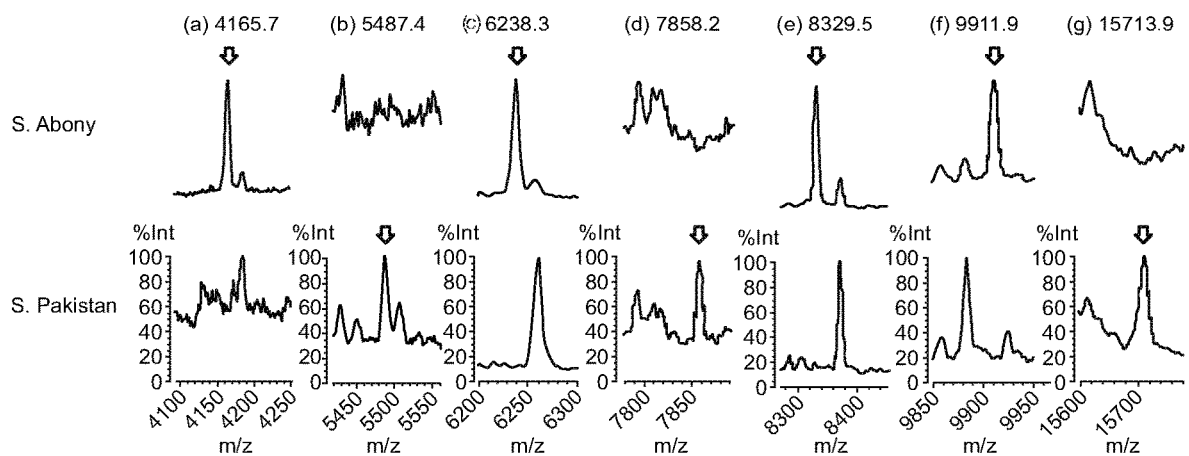
FIG. 3 shows mass spectra obtained for two samples which respectively contained bacterial bodies of *Abony* and *Pakistan* which are two serotypes of *Salmonella* bacteria (first group), with each mass spectrum including one of the seven peaks shown in Table 2 which satisfy the second criterion, among the peaks in the mass spectra.
Figure 4:
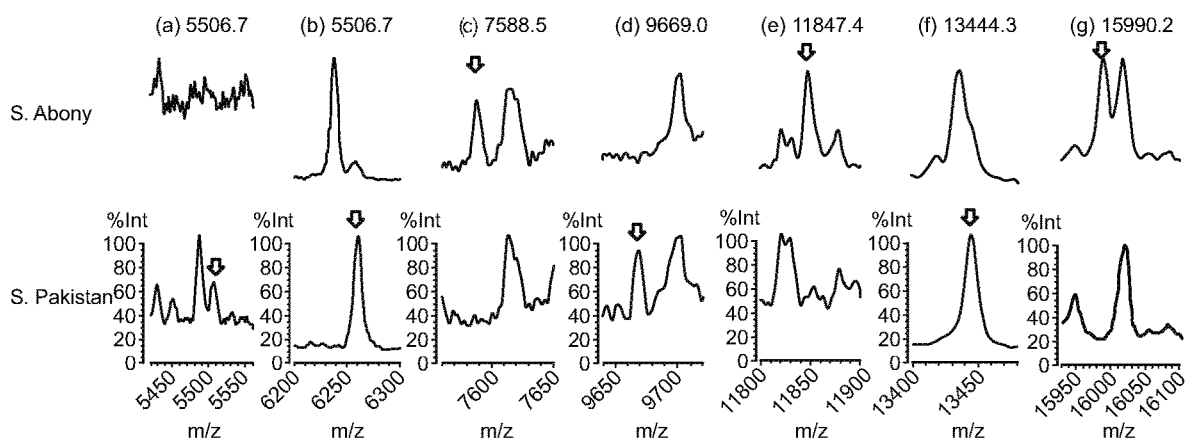
FIG. 4 shows mass spectra obtained for two samples which respectively contained bacterial bodies of *Abony* and *Pakistan* which are two serotypes of *Salmonella* bacteria (first group), with each mass spectrum including one of the seven peaks shown in Table 2 which do not satisfy the second criterion but satisfy the first criterion, among the peaks in the mass spectra.

FIG. 3 shows the mass spectra, where each mass spectrum covers an m/z range including 4165.7, 5487.4, 6238.3, 7858.2, 8329.5, 9911.9 or 15713.9 among the m/z values of the peaks which satisfy the second criterion (i.e., the m/z values shown in Table 2). FIG. 4 shows the mass spectra, where each mass spectrum covers an m/z range including 5506.7, 6261.2, 7588.5, 9669.0, 11847.4, 13444.3 or 15990.2 among the m/z values of the peaks which satisfy the first criterion but do not satisfy the second criterion. In both FIG. 3 and FIG. 4, the upper shows the mass spectrum for *S. abony*, and the lower shows the mass spectrum for *S. pakistan*. The arrows in FIGS. 3 and 4 indicate the extracted peaks.

As shown in FIGS. 3 and 4, each of the peaks extracted based on the first and second criteria is only present in either the mass spectrum for *S. abony* or the mass spectrum for *S. pakistan*. Therefore, which of *S. abony* and *S. pakistan* is the serotype of the *Salmonella* bacteria contained in the sample can be determined by the presence or absence of the peak. That is to say, the serotype of the *Salmonella* bacteria can be identified. In particular, the use the peaks which satisfy the second criterion enables a more correct identification of the serotype since those peaks have higher S/N ratios than the peaks which satisfy only the first criterion, and since those peaks have no nearby peaks. It should be noted that any one of the peaks at the 42 mass-to-charge ratios (m/z values) shown in Table 1 can be solely used as a marker peak for identifying the serotype of the *Salmonella* bacteria contained in a sample, although using peaks at a plurality of mass-to-charge ratios (m/z values) as marker peaks enables a more accurate identification of the serotype of the *Salmonella* bacteria contained in a sample.

Thus, which of the two serotypes of *Salmonella* bacteria belonging to the first group (*S. abony* and *S. pakistan*) was the actual serotype could be determined by checking the state of the peak detection at the mass-to-charge ratios (m/z values) in Table 1 or 2.

(2) Second Group

The state of the peak detection at the previously listed mass-to-charge ratios (m/z values) was checked on the mass spectra obtained from three samples which respectively contained any one of the three kinds of *Salmonella* bacteria belonging to the second group (*S. minnesota, S. infantis* and *S. brandenburg*). The state of the detection was as shown in Tables 3 and 4.

Figure 5:
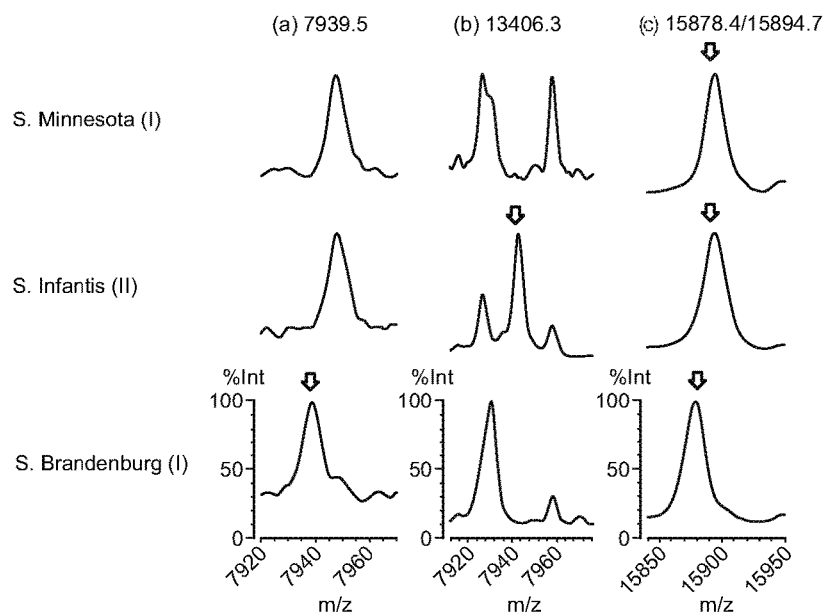
FIG. 5 shows mass spectra obtained for three samples which respectively contained bacterial bodies of *Minnesota, Infantis* and *Brandenburg* which are three serotypes of *Salmonella* bacteria (second group), with each mass spectrum including one of the three peaks shown in Table 4 which satisfy the second criterion. among the peaks in the mass spectra.

FIG. 5 shows the mass spectra, where each mass spectrum covers an m/z range including 7939.5, 13406.3 or 15878.4/15894.7 among the m/z values of the peaks which satisfy the second criterion (i.e., the m/z values shown in Table 4).

Figure 6:
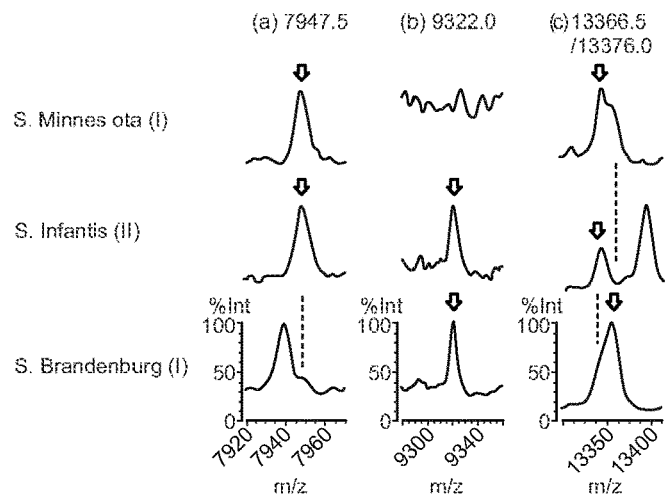
FIG. 6 shows mass spectra obtained for three samples which respectively contained bacterial bodies of *Minnesota, Infantis* and *Brandenburg* which are three serotypes of *Salmonella* bacteria (second group), with each mass spectra including one of the three peaks shown in Table 3 which do not satisfy the second criterion but satisfy the first criterion, among the peaks in the mass spectra.

FIG. 6 shows the mass spectra, where each mass spectrum covers an m/z range including 7947.5, 9322.0 or 13366.5/13376.0 among the mass-to-charge ratios (m/z values) of the peaks which satisfy the first criterion but do not satisfy the second criterion. In both FIG. 5 and FIG. 6, the upper shows the mass spectrum obtained for the sample containing *S. minnesota*, the middle shows the mass spectrum obtained for the sample containing *S. infantis*, and the lower shows the mass spectrum obtained for the sample containing *S. brandenburg*. The arrows in FIGS. 5 and 6 indicate the extracted peaks.

As shown in FIGS. 5 and 6, each of the peaks extracted based on the first and second criteria is present or absent on only one of the mass spectra obtained from the three samples which respectively contained *S. minnesota, S. infantis* and *S. brandenburg*. Therefore, which of *S. minnesota, S. infantis* and *S. brandenburg* is the serotype of the *Salmonella* bacteria contained in the sample can be determined by the presence or absence of the peak. That is to say, the serotype of the *Salmonella* bacteria can be identified. In particular, the use the peaks which satisfy the second criterion enables a more correct identification of the serotype since those peaks have higher S/N ratios than the peaks which satisfy only the first criterion, and since those peaks have no nearby peaks.

It should be noted that any one of the peaks at the 35 mass-to-charge ratios (m/z values) shown in Table 3 can be solely used as a marker peak for identifying the serotype of the *Salmonella* bacteria contained in a sample, although using peaks at a plurality of mass-to-charge ratios (m/z values) as marker peaks enables a more accurate identification of the serotype of the *Salmonella* bacteria contained in a sample.

Thus, which of the three serotypes of *Salmonella* bacteria belonging to the second group (*S. minnesota, S. infantis* and *S. brandenburg*) was the actual serotype could be determined by checking the state of the peak detection at the mass-to-charge ratios (m/z values) in Table 3 or 4.

(3) Third Group

The state of the peak detection at the previously listed mass-to-charge ratios (m/z values) was checked on the mass spectra obtained from two samples which respectively contained one of the two kinds of *Salmonella* bacteria belonging to the third group (*S. schwarzengrund* and *S. montevideo*). The state of the detection was as shown in FIGS. 7 and 8.

Figure 7:
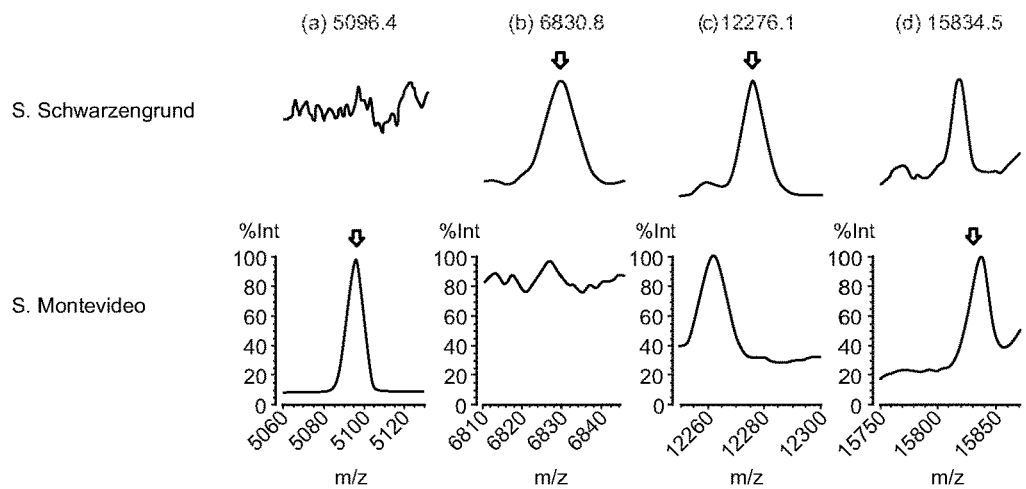
FIG. 7 shows mass spectra obtained for two samples which respectively contained bacterial bodies of Schwarzengrund and Montevideo which are two serotypes of *Salmonella* bacteria (third group), with each mass spectrum including one of the four peaks shown in Table 6 which satisfy the second criterion, among the peaks in the mass spectra.

FIG. 7 shows the mass spectra, where each mass spectrum covers an m/z range including 5096.4, 6830.8, 12276.1 or 15834.5 among the m/z values of the peaks which satisfy the second criterion (i.e., the m/z values shown in Table 6).

Figure 8:
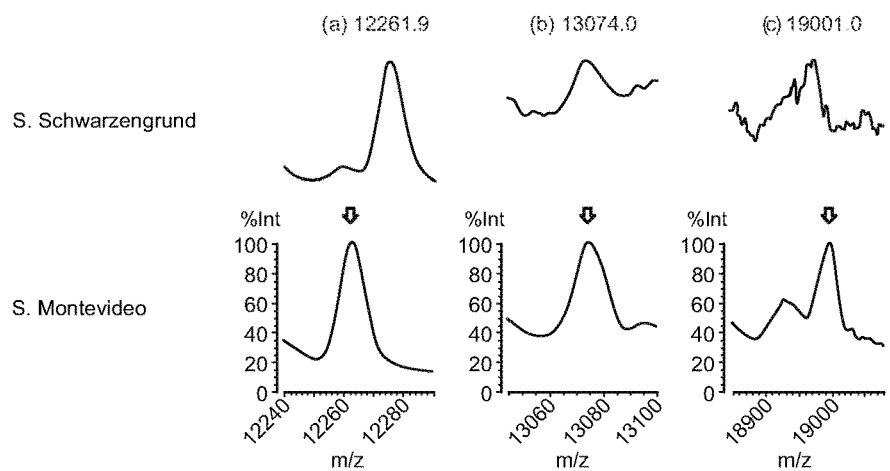
FIG. 8 shows mass spectra obtained for two samples which respectively contained bacterial bodies of Schwarzengrund and Montevideo which are two serotypes of *Salmonella* bacteria (third group), with each mass spectrum including one of the three peaks shown in Table 5 which do not satisfy the second criterion but satisfy the first criterion, among the peaks in the mass spectra.

FIG. 8 shows the mass spectra, where each mass spectrum covers an m/z range including 12261.9, 13074.0 or 19001.0 among the m/z values of the peaks which satisfy the first criterion but do not satisfy the second criterion. In both FIG. 7 and FIG. 8, the upper shows the mass spectrum obtained for the sample containing *S. schwarzengrund*, and the lower shows the mass spectrum obtained for the sample containing *S. montevideo*. The arrows in FIGS. 7 and 8 indicate the extracted peaks.

As shown in FIGS. 7 and 8, each of the peaks extracted based on the first and second criteria is only present on either the mass spectrum of the sample containing *S. schwarzengrund* or the mass spectrum of the sample containing *S. montevideo*. Therefore, which of *S. schwarzengrund* and *S. montevideo* is the serotype of the *Salmonella* bacteria contained in the sample can be determined by the presence or absence of the peak. That is to say, the serotype of the *Salmonella* bacteria can be identified. In particular, the use the peaks which satisfy the second criterion enables a more correct identification of the serotype since those peaks have higher S/N ratios than the peaks which satisfy only the first criterion, and since those peaks have no nearby peaks. It should be noted that any one of the peaks at the 11 mass-to-charge ratio (m/z) values shown in Table 5 can be solely used as a marker peak for identifying the serotype of the *Salmonella* bacteria contained in a sample, although using peaks at a plurality of mass-to-charge ratio (m/z) values as marker peaks enables a more accurate identification of the serotype of the *Salmonella* bacteria contained in a sample.

Thus, which of the two serotypes of *Salmonella* bacteria belonging to the third group (*S. schwarzengrund* and *S. montevideo*) was the actual serotype could be determined by checking the state of the peak detection at the mass-to-charge ratios (m/z values) in Table 5 or 6.

Modes of Invention

A person skilled in the art can understand that the previously described illustrative embodiments are specific examples of the following modes.

(Clause 1) A method for analyzing a microorganism according to one mode is a method for analyzing a microorganism including:

an identification step for determining which of *Abony* and *Pakistan* which are two serotypes of *Salmonella* bacteria is contained in a sample which contains either *Abony* or *Pakistan*, based on the presence or absence of a peak (or peaks) at a predetermined mass-to-charge ratio (or ratios) in a mass spectrum obtained by a mass spectrometric analysis of the sample, where the value or values of the predetermined mass-to-charge ratio or ratios are selected from the group consisting of 3028, 3119, 4166, 5487, 5507, 5924, 6011, 6095, 6238, 6261, 6369, 6720, 6725, 6933, 7272, 7453, 7480, 7589, 7858, 7903, 8053, 8129, 8330, 8461, 8536, 8546, 8634, 8687, 9669, 9912, 10956, 11499, 11506, 11847, 12276, 13366, 13373, 13435, 13444, 15714, 15803 and 15990 as well as any combination of these values.

(Clause 2) In the method for analyzing a microorganism described in Clause 1, the value or values of the predetermined mass-to-charge ratio or ratios are specifically selected from the group consisting of 3119, 4166, 5487, 6238, 6720, 7858, 8330, 8536, 8687, 9912, 12276, 15714, 15803 and 15990 as well as any combination of these values.

According to the method for analyzing a microorganism described in Clause 1, if it is previously known that the serotype of the *Salmonella* bacteria contained in a sample is one of the two serotypes (*Abony* and *Pakistan*), it is possible to determine which of *Abony* and *Pakistan* is the actual serotype. According to the method for analyzing a microorganism described in Clause 2, which of *Abony* and *Pakistan* is the actual serotype can be more correctly determined.

(Clause 3) A method for analyzing a microorganism according to another mode is a method for analyzing a microorganism including:

an identification step for determining which of *Minnesota, Infantis* and *Brandenburg* which are three serotypes of *Salmonella* bacteria is contained in a sample which contains *Minnesota, Infantis* or *Brandenburg*, based on the presence or absence of a peak (or peaks) at a predetermined mass-to-charge ratio (or ratios) in a mass spectrum obtained by a mass spectrometric analysis of the sample, where the value or values of the predetermined mass-to-charge ratio or ratios are selected from the group consisting of 6094, 6483, 6689, 6719, 6872, 7858, 7940, 7948, 9322, 10667, 10990, 11808, 11821, 11848, 11857, 12209, 13366, 13376, 13406, 13445, 13476, 14882, 15716, 15803, 15878, 15895, 15991, 17713, 17735, 17813, 17835, 18972, 19127, 20766 and 20838 as well as any combination of these values.

(Clause 4) In the method for analyzing a microorganism described in Clause 3, the value or values of the predetermined mass-to-charge ratio or ratios are specifically selected from the group consisting of 6483, 7940, 10990, 11808, 11821, 11848, 11857, 12209, 13406, 13445, 15803, 15878, 15895, 17713 and 17735.

According to the method for analyzing a microorganism described in Clause 3, if it is previously known that the serotype of the *Salmonella* bacteria contained in a sample is one of the three serotypes (*Minnesota, Infantis* and *Brandenburg*), it is possible to determine which of *Minnesota, Infantis* and *Brandenburg* is the actual serotype. According to the method for analyzing a microorganism described in Clause 4, which of *Minnesota, Infantis* and *Brandenburg* is the actual serotype can be more correctly determined.

(Clause 5) A method for analyzing a microorganism according to still another mode is a method for analyzing a microorganism including:

an identification step for determining which of Schwarzengrund and Montevideo which are two serotypes of *Salmonella* bacteria is contained in a sample which contains either Schwarzengrund or Montevideo, based on the presence or absence of a peak (or peaks) at a predetermined mass-to-charge ratio (or ratios) in a mass spectrum obtained by a mass spectrometric analysis of the sample, where the value or values of the predetermined mass-to-charge ratio or ratios are selected from the group consisting of 5096, 6699, 6733, 6830, 9034, 12262, 12276, 13074, 15820, 15835 and 19001 as well as any combination of these values.

(Clause 6) In the method for analyzing a microorganism described in Clause 5, the value or values of the predetermined mass-to-charge ratio or ratios are specifically selected from the group consisting of 5096, 6699, 6733, 6830, 9034, 12276, 15820 and 15835 as well as any combination of these values.

According to the method for analyzing a microorganism described in Clause 5, if it is previously known that the serotype of the *Salmonella* bacteria contained in a sample is one of the two serotypes (Schwarzengrund and Montevideo), it is possible to determine which of Schwarzengrund and Montevideo is the actual serotype. According to the method for analyzing a microorganism described in Clause 6, which of Schwarzengrund and Montevideo is the actual serotype can be more correctly determined.

(Clause 7) The second mode is a program for making a computer execute the step described in one of Clauses 1-6.

The invention claimed is:

1. A method for analyzing a microorganism, comprising:
an identification step for determining which of Schwarzengrund and Montevideo which are two serotypes of *Salmonella* bacteria is contained in a sample which contains either Schwarzengrund or Montevideo, based on presence or absence of a peak or peaks at a predetermined mass-to-charge ratio or ratios, in a mass spectrum obtained by a mass spectrometric analysis of the sample,
where the value or values of the predetermined mass-to-charge ratio or ratios are selected from the group consisting of 5096, 6699, 6733, 6830, 9034, 12262, 12276, 13074, 15820, 15835 and 19001 as well as any combination of these values.

2. The method for analyzing a microorganism according to claim 1, wherein the value or values of the predetermined mass-to-charge ratio or ratios are selected from the group consisting of 5096, 6699, 6733, 6830, 9034, 12276, 15820 and 15835 as well as any combination of these values.

3. A non-transitory computer readable medium recording a program for making a computer execute the step described in claim 1.

* * * * *